United States Patent [19]

Sakamoto et al.

[11] Patent Number: 4,973,576
[45] Date of Patent: Nov. 27, 1990

[54] BISPHOPHONIC ACID DERIVATIVES AND PHARMACEUTICAL COMPOSITIONS CONTAINING THE SAME

[75] Inventors: Shuichi Sakamoto; Makoto Takeuchi; Yasuo Isomura, all of Tokyo; Kunihiro Niigata; Tetsushi Abe, both of Saitama; Kousei Kawamuki; Masafumi Kudou, both of Tokyo, all of Japan

[73] Assignee: Yamanouchi Pharmaceutical Co., Ltd., Tokyo, Japan

[21] Appl. No.: 165,741

[22] Filed: Mar. 9, 1988

[30] Foreign Application Priority Data

Mar. 10, 1987 [JP] Japan ................... 62-54913
Sep. 30, 1987 [JP] Japan ................... 62-248555
Oct. 19, 1987 [JP] Japan ................... 62-265097
Oct. 19, 1987 [JP] Japan ................... 62-265098
Dec. 8, 1987 [JP] Japan ................... 62-311525
Dec. 15, 1987 [JP] Japan ................... 62-318077
Dec. 24, 1987 [JP] Japan ................... 62-327879
Dec. 24, 1987 [JP] Japan ................... 62-327646

[51] Int. Cl.$^5$ ..................... A61K 31/675; C07F 9/653
[52] U.S. Cl. ......................... 514/92; 548/119
[58] Field of Search ................... 548/119; 514/92

[56] References Cited

U.S. PATENT DOCUMENTS 4,687,767 8/1987 Bosies et al. ............... 514/89

FOREIGN PATENT DOCUMENTS 186405 7/1986 European Pat. Off. .
258618 3/1988 European Pat. Off. .
274347 7/1988 European Pat. Off. .
89293 7/1980 Japan .

Primary Examiner—Richard L. Raymond
Attorney, Agent, or Firm—Burgess, Ryan & Wayne

[57] ABSTRACT

"Novel bisphosphonic acid derivatives, and a bone resorption-inhibitor and an anti-arthritis containing a bisphosphonic acid derivative represented by the formula (I):

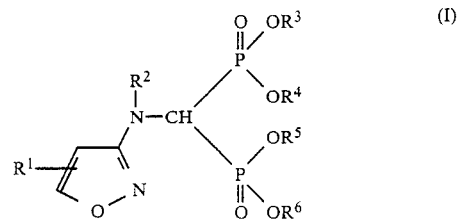

wherein
$R^2$ represents a hydrogen atom, an alkyl group, etc.,
$R^2$ represents a hydrogen atom or a lower alkanoyl group,
$R^3$, $R^4$, $R^5$ and $R^6$ may be the same or different, each represents a hydrogen atom or lower alkyl group."

15 Claims, No Drawings

BISPHOPHONIC ACID DERIVATIVES AND PHARMACEUTICAL COMPOSITIONS CONTAINING THE SAME

BACKGROUND OF THE INVENTION

1. Field of the Invention

The present invention relates to new bisphosphonic acid derivatives as represented by the following formula (I') or pharmaceutically acceptable salts thereof.

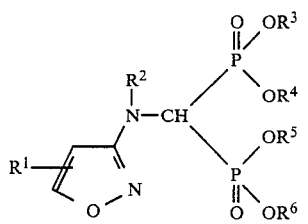
(I')

in which $R^1$ represents a hydrogen atom, an alkyl group having from 1 to 10 carbon atoms, a cycloalkyl group having from 3 to 10 carbon atoms, a phenyl group, an alkenyl group having from 2 to 10 carbon atoms which may be substituted by a phenyl group or a phenyl substituted alkyl group having from 1 to 5 carbon atoms which may be substituted by an alkoxy group having from 1 to 5 carbon atoms;

$R^2$ represents a hydrogen atom or an alkanoyl group having from 2 to 6 carbon atoms;

$R^3$, $R^4$, $R^5$ and $R^6$ may be the same or different, each represents a hydrogen atom or an alkyl group having from 1 to 5 carbon atoms; provided that when $R^1$ represents a methyl group, an ethyl group, an isopropyl group or a tert-butyl group, at least one of $R^2$, $R^3$, $R^4$, $R^5$ and $R^6$ represents a substituent other than hydrogen atom.

The present invention also relates to a bone resorption-inhibitor and an anti-arthritis containing, as an active ingredient, a bisphosphonic acid derivative as represented by the following formula (I) or a pharmaceutically acceptable salt thereof.

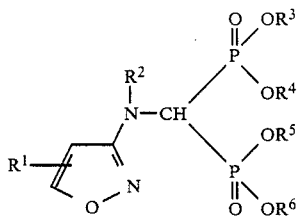
(I)

in which $R^1$ represents a hydrogen atom, an alkyl group having from 1 to 10 carbon atoms, a cycloalkyl group having from 3 to 10 carbon atoms, a phenyl group, an alkenyl group having from 2 to 10 carbon atoms which may be substituted by a phenyl group or a phenyl substituted alkyl group having from 1 to 5 carbon atoms which may be substituted by an alkoxy group having from 1 to 5 carbon atoms;

$R^2$ represents a hydrogen atom or an alkanoyl group having from 2 to 6 carbon atoms;

$R^3$, $R^4$, $R^5$ and $R^6$ may be the same or different, each represents a hydrogen atom or an alkyl group having from 1 to 5 carbon atoms.

DESCRIPTION OF THE RELATED ART

Hitherto, various compounds have been synthesized as bisphosphonic acid derivatives, and there may be mentioned Japanese Patent Application (OPI) No. 89293/80 (the term "OPI" as used herein means a "published unexamined Japanese patent application") which discloses compounds having an aminomethylene-bisphosphonic acid residue as bonded at the 3-position of a substituted isoxazolyl group, like the compounds of the present invention.

The said Japanese Patent Application (OPI) No. 89293/80 (hereinafter referred to as "(OPI) No. 89293/80") mentions bisphosphonic acid series compounds of a formula:

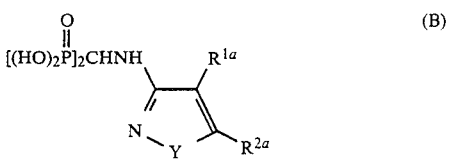
(B)

in which $R^{1a}$ represents a hydrogen atom, an alkyl group or a halogen atom;

$R^{2a}$ represents a hydrogen atom or an alkyl group; and

Y represents an oxygen atom or an NH group.

However, the substituted isoxazolylaminomethylene-bisphosphonic acid derivatives which are concretely illustrated in the examples of (OPI) No. 89293/80 are those having methyl group, ethyl group, isopropyl group or tert-butyl group as the alkyl group for the substituent on the isoxazolyl group, and further, only free bisphosphonic acids are limitatedly illustrated therein.

Specifically, only the compounds of a general formula (I''):

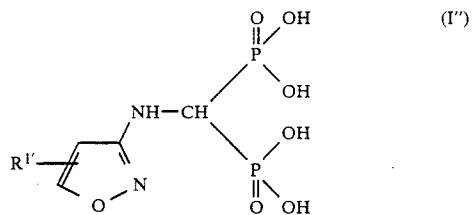
(I'')

in which $R^{1'}$ represents a methyl group, an ethyl group, an isopropyl group or a tert-butyl group, which may correspond to the compounds of the above-mentioned formula (I') of the present invention, are concretely illustrated in (OPI) No. 89293/80.

Further, (OPI) No. 89293/80 mentions that the substituted isoxazolylaminomethylene-bisphosphonic acid derivatives can be used as agricultural chemicals, especially as herbicide, but this is quite silent on the usability of the said derivatives as medicines.

Ordinary bones are living tissues which participate in resorption and precipitation of calcium for maintaining a constant inorganic equilibrium in a living body. In growing bones, the inorganic precipitation exceeds the inorganic resorption, but the bone resorption often exceeds the bone precipitation (ossification) in special diseases of some kinds, which would induce hypercalcemia, Paget's disease, etc. Hitherto, 1-hydroxyethylidene-1,1-bisphosphonic acid (etidronate), dichloromethylene-bisphosphonic acid (chlodronate), etc. have been used as remedial medicines for the diseases caused by the bone resorption, but these are insufficient from the viewpoint that the activity is not high and they have harmful side effects. Accordingly, sufficient medicines for the diseases are unknown up to the present.

Arthritides are inflammatory diseases of articulations, and the main diseases include rheumatic arthritis and the analogous diseases with articular inflammation.

Above all, the rheumatic arthritis is called a rheumatiod arthritis, which is a cryptogenetic chronic polyarthritis where the main lesion resides in the inflammatory lesion in the synovial membrane in the intracapsular layer. Arthritides such as rheumatic arthritis, etc. are progressive diseases which cause articular disorders such as articular deformation, ankylosis, etc. Accordingly, if these are deteriorated with no effective remedial treatment, these would often cause severe somatic disorders in some cases.

Various medicines have heretofore been used for the medicinal treatment for these arthritides, including, for example, steroids such as cortisone and other adrenocortical hormones; non-steriod series anti-inflammatory agents such as aspirin, piroxicam, indometacin, etc.; gold agents such as gold thiomalate, etc.; anti-rheumatic agents such as chloroquine preparations, D-penicillamine, etc.; anti-gouty agents such as colchicine, etc.; immunosuppressants such as cyclophosphamide, azathioprine, methotrexate, levamisole, etc.

However, these medicines have various problems in that they have harmful side-effects which are serious or which would make the long use difficult, or the effect is not sufficient, or they are not effective to the already expressed arthritides, etc.

Accordingly, in the clinical medicine for arthritides, the actual circumstances are that the provision of chemical medicines which are less toxic and which have an excellent preventive and remedial activity against arthritides is strongly desired.

The present inventors found that the compounds as represented by the above-mentioned formula (I') and salts thereof are new and additionally found, as a result of animal tests, that the compounds as represented by the above-mentioned formula (I) and salts thereof unexpectedly have a bone resorption-inhibitor activity to be able to inhibit hypercalcemia caused by bone resorption as well as have an excellent anti-arthritic activity, and accordingly have hereby achieved the present invention.

SUMMARY OF THE INVENTION

Specifically, the present invention provides the new bisphosphonic acid derivatives as represented by the above-mentioned formula (I') and salts thereof. Additionally, it provides a bone resorption-inhibitor as well as an anti-arthritis containing, as an active ingredient, the bisphosphonic acid derivative as represented by the above-mentioned formula (I) or its salt. (The derivatives of the formula (I) and their salts include the bisphosphonic acid derivatives of the formula (I') and their salts and the bisphosphonic acid derivatives of the formula (I'') and their salts).

In the groups in the general formulae as herein referred to, the alkly group having from 1 to 5 carbon atoms (hereinafter this is described as "lower alkyl group") is a linear or branched carbon chain. Accordingly, the lower alkyl group includes a methyl group, an ethyl group, a propyl group, an isopropyl group, a butyl group, an isobutyl group, a sec-butyl group, a tert-butyl group, a pentyl (amyl) group, an isopentyl group, a neopentyl group, etc. The alkyl group having from 1 to 10 carbon atoms in the general formulae is a linear or branched carbon chain, which includes, in addition to the above-mentioned examples for the lower alkyl group, an n-hexyl group, an n-heptyl group, an n-octyl group, an n-nonyl group, an n-decyl group, an isoheptyl group, a 2-ethylbutyl group, a 2-ethylpentyl group, a 4-ethylheptyl group, etc. The cycloalkyl group having from 3 to 10 carbon atoms includes, for example, a cyclopropyl group a cyclobutyl group, a cyclopentyl group, a cyclooctyl group, a cyclodecyl group, etc. The alkenyl group having from 2 to 10 carbon atoms means a linear or branched hydrocarbon group, typically including a vinyl group, an allyl group, an isopropenyl group, a 2-butenyl group, a 2-methyl-2-propenyl group, a 3-pentenyl group, a 4-methyl-3-pentenyl group, a 4-methyl-3-hexenyl group, a 4-ethyl-3-hexenyl group, etc. These alkenyl groups may optionally be substituted by a phenyl group. Typical phenylalkenyl groups include a styryl group, a 3-phenyl-2-propenyl group, a 4-phenyl-2-butenyl group, etc.

The "phenyl substituted alkyl group having from 1 to 5 carbon atoms which may be substituted by an alkoxy group having from 1 to 5 carbon atoms (hereinafter this is described as "lower alkoxy group")" includes a benzyl group, a phenethyl group, a phenylpropyl group, a phenylbutyl group, etc. which are unsubstituted or substituted by a methoxy group, an ethoxy group, a propoxy group, a butoxy group, a pentyloxy group, an iso-propoxy group, an iso-butoxy group, an iso-pentyloxy group, a tert-pentyloxy group, etc. The said lower alkoxy group may be substituted in any position on the phenyl group.

The "alkanoyl group having from 2 to 6 carbon atoms (hereinafter this is described as "lower alkanoyl group")" includes, for example, an acetyl group, a propionyl group, a butanoyl group, etc. Among the said substituents, $R^1$ is preferably a lower alkyl group or a cycloalkyl group. This is more preferably a methyl group, a pentyl group, a cyclopropyl group, etc. The group $R^1$ may be substituted in the 4- or 5-position on the isoxazole ring in the above-mentioned general formulae. The compounds of the present invention include tetraesters in which $R^3$ to $R^6$ are all lower alkyl groups as well as monoesters, diesters and triesters in which one to three of $R^3$ to $R^6$ is(are) lower alkyl group(s).

The free phosphonic acids of the present invention can form the corresponding salts. Accordingly, the active ingredients of the present invention include pharmaceutically acceptable salts of the compounds of the formula (I). Concretely, there may be mentioned salts with inorganic bases, for example, salts with alkali metals such as sodium, potassium, etc., and salts with alkaline earth metals such as calcium, magnesium, etc.; ammonium salts; salts with organic bases such as methylamine, ethylamine, dimethylamine, diethylamine, trimethylamine, triethylamine, cyclohexylamine, ethanolamine, diethanolamine, etc.; and salts with basic amino acids such as lysine, ornithine, etc.

MANUFACTURE METHOD:

The compounds of the formula (I) of the present invention can be manufactured in accordance with the following reaction formulae.

First Method:

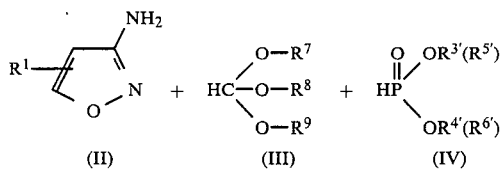

Second Method:

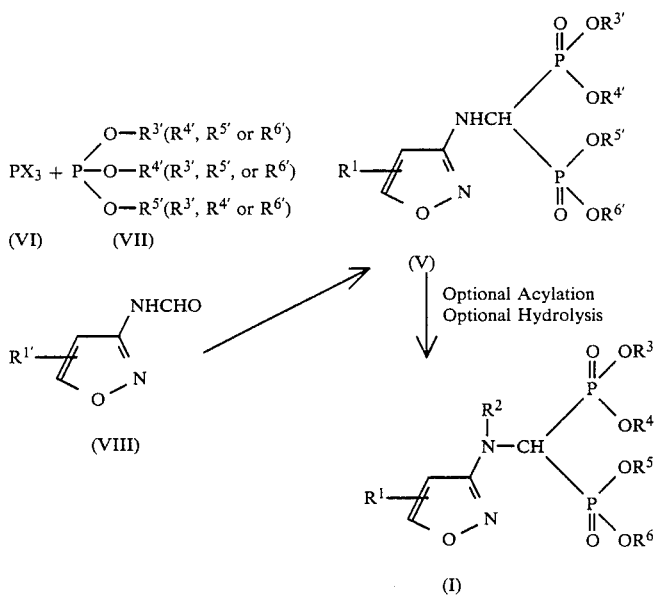

In these formulae, $R^1$, $R^2$, $R^3$, $R^4$, $R^5$ and $R^6$ are the same significance as above, $R^{3'}$, $R^{4'}$, $R^{5'}$ and $R^{6'}$ may be the same or different, each represents an alkyl group having from 1 to 5 carbon atoms, $R^7$, $R^8$ and $R^9$ may be the same or different, each represents an alkyl group having from 1 to 5 carbon atoms, and X represents a halogen atom.

FIRST METHOD:

In this method, the respective reaction components of a 3-aminoisoxazole (II), a lower alkyl ortho-formate (III) and a dialkyl phosphite (IV) are blended each in the corresponding reaction amount or excessive amount of (IV) and reacted under heating. A reaction solvent is not specifically required. The reaction is performed generally at 100° to 200° C., preferably at 150° C. or so, for 10 to 60 minutes.

For isolating and purifying the thus obtained reaction product (V), for example, the reaction mixture is purified on a silicagel column with a mixed solvent of methanol-chloroform.

In the reaction of the 3-aminoisoxazole (II) and the lower alkyl ortho-formate (III), an iminoether intermediate of a formula:

$$R^{1'}\text{—}\underset{O\text{—}N}{\bigg\langle}\text{—}N=\overset{H}{\underset{|}{C}}\text{—}O\text{—}R^7\ (R^8\text{ or }R^9)$$

(wherein $R^1$, $R^7$ and $R^8$ are the same significance as above.) may be isolated.

The iminoether intermediate can be further reacted with the dialkyl phosphite (IV) to give the compound (V).

For isolation and purification of the thus obtained reaction product, for example, the reaction mixture is directly purified by silica gel column chromatography, or alternatively, this is washed with water in the form of a chloroform solution, and after the solvent was distilled out, the resulting residue can be purified by silica gel column chromatography.

For manufacture of the final products in which $R^2$ represents a lower alkanoyl group, the compound (V) (especially the ester thereof) is acylated. For the acylation, the compound (V) may be reacted with a reaction-equivalent amount or excessive amount of an acylating agent directly or in a solvent. As the acylating agent can be used acid anhydrides, acid halides, etc. As the reaction solvent can be used benzene, toluene, diglyme, etc. The reaction is desirably carried out under heating.

The bisphosphonates can be converted into the corresponding bisphosphonic acids by hydrolysis. The hydrolysis is generally carried out by heating under reflux in a concentrated hydrochloric acid. Alternatively, the bisphosphonates can be treated with a strong acid or a trimethylsilyl halide in a water-free solvent. For the method, in general, a commercial anhydrous hydrobromic acid in acetic acid can be used directly or in the form of a pertinently diluted solution, or a solution of an iodide trimethylsilane as dissolved in a solvent such as carbon tetrachloride, dimethylformamide, chloroform, toluene, etc. can be used. Regarding the temperature, the hydrolysis is carried out with cooling or heating. For example, when the ester is hydrolyzed with a trimethylsilyl halide with cooling at $-10°$ C. or lower, a partially hydrolyzed product is obtained.

When the bisphosphonic acid is to be converted into its salt, the acid is treated with a base such as sodium hydroxide, potassium hydroxide, ammonia or organic amines, etc. in a conventional manner.

SECOND METHOD:

In this method, a mixture solution comprising 1 mol. of phosphorus trihalogenide (VI) and excessive amount, preferably 2 to 10 mol. of trialkyl phosphite (VII) is first reacted, for example, at 40° to 100° C., preferably at 60° to 80° C., for 15 to 30 minutes, and then a substituted isoxazole-3-formamide (VIII) is added to the resulting mixture solution and heated, for example, at 40° to 100° C., preferably at 60° to 80° C., for several hours. The progress of the reaction can easily be confirmed by TLC (thin layer chromatography, with developer system of chloroform-methanol). After the completion of the reaction, the excess trialkyl phosphite is removed out by distillation.

Then, the isolation and purification of the obtained product, and the acylation and hydrolysis can be performed by the same manner as the first method.

In addition to the above-mentioned manufacture methods, the compounds (I) can be produced by any other various methods. For instance, in accordance with the method described in Japanese Patent Application (OPI) No. 89293/80, a free bisphosphonic acid is first obtained and then esterified or is subjected to salt-formation reaction.

The isolation and purification of the final products (I) can be carried out by conventional chemical treatments which include extraction, crystallization, recrystallization, various chromatography operations, etc.

EFFECT OF THE INVENTION:

The compounds (I) and their salts provided by the present invention have a bone resorption-inhibitory action and also have an action of inhibiting hypercalcemia caused by bone resorption. Accordingly, the compounds (I) and their salts of the present invention are useful as a remedy or preventive to hypercalcemia caused by bone resorption, Paget's disease, metastatic osteocarcinoma, osteopsathrosis, sthenic bone resorption to follow inflammatory arthritides such as chronic rheumatoid arthritis, etc. In addition, these are recognized to have excellent anti-inflammatory action and sedative and analgesic action. Further, the anti-arthritic action of the compounds (I) of the present invention was demonstrated and confirmed by the preventive and remedial activity to adjuvant-induced arthritis.

The adjuvant-induced arthritis is widely utilized as a study model for arthritides in this technical field, as this results in polyarthritis chronica which is analogous to human rheumatic arthritis.

As mentioned hereinafter, the compounds provided by the present invention were demonstrated and confirmed to have prophylactic and therapeutic actions in the adjuvant arthritis. Although it is not clarified by what function and mechanism the compounds could have the anti-arthritic action, it is presumed that the compounds provided by the present invention could have a direct inhibitory action at least to the inflammatory symptoms of arthritides, in view of the reported fact that conventional immunosuppressants and immunomodulators could not be recognized to be effective on already expressed arthritides, while glucocorticosteroids could have an anti-arthritic action in both the prophylactic and the therapeutic experiment for arthritides.

Accordingly, the compounds can be applied to all arthritides which cause inflammation. Diseases for which the compounds are efficacious include rheumatic arthritic and the arthritides which cause inflammation, for example, cryptogenetic polyarthritides such as juvenile rheumatoid arthritis (including Still's disease), tetanic myelitis, psoriatic arthritis, Reiter's syndrome, etc.; rheumatic fever (acute rheumatic arthritis); diseases to cause arthritic symptom, amoung gouty and metabolic articular diseases such as gout, pseudogout, Wilson's diseases, etc.; diseases to cause arthritic symptom, among medical diseases except metabolic diseases, which are often accompanied by complicated arthritides, for example, pulmonary hypertrophic arthritis, sarcoidosis, ulcerative colitis, regional ileitis, Whipple's disease, liver diseases, hemophilic arthritis, hemoglobinopathy, hemochromatosis, accessory thyroid hyperergasia, hypothyroidism, etc.; diseases to cause arthritic symptom in collagen diseases (except rheumatic arthritis) such as systemic scleroderma (dermatosclerosis), systemic lupus erythematous, etc.; diseases to cause arthritic symptom in Bechcet's syndrome; traumatic arthritides and the analogous diseases thereof; infectious arthritides such as suppurative arthritis, etc. Experimental test methods and results are mentioned hereunder so as to support the pharmacological effect of the compounds (I) and their salts provided by the present invention.

(1) INHIBITORY EFFECT ON HYPERCALCEMIA:

Rats of hypercalcemia induced by administration of parathyroid hormone (hereinafter referred to as "PTH") were used, and the decrement of the serum calcium amount by administration of the compound was measured.

TEST METHOD:

30 $\mu g/kg$ of human 1–34 PTH (manufactured by Peptide Laboratory) which was dissolved in a 0.1% BSA (bovine serum albumin)-containing physiological saline (content of the PTH is 6 $\mu g/ml$) was intravenously injected in an amount of 30 $\mu g/kg$ (5 ml/kg as the solution) to 5-week male Wistar rats which had been fasting for 20 hours. Only 0.1% BSA-containing physiological saline was injected to the normal control group in the same manner. 45 minutes after the PTH injection, the rats were etherized and then subjected to celiotomy, whereby the blood was collected from the abdominal cava with a vacuum blood-collecting tube. The blood collected was immediately centrifuged by 3000 rpm, at 4° C. for 10 minutes to isolate the serum. The ionized calcium ($Ca^{++}$) concentration in the serum was immediately measured with a $Ca^{++}$meter (Sera 250, manufactured by Horiba Manufacturing Co.).

The compounds of the present invention were dissolved using sodium hydroxide and hydrochloric acid, in physiological saline (pH 7.4), for subcutaneous administration, in such amounts that the dose amounted to 2 ml/kg, and for oral administration, in distilled water (pH 7.4) so that the dose amounted to 5 ml/kg. They were administered 24 or 72 hours before the PTH injection. A physiological saline or a distilled water was administered to the normal control group and the control group, in the same manner. Salmon calcitonin (SCT, manufactured by Armour Co.) was dissolved in physiological saline so that the dose amounted to 2 ml/kg, and then subcutaneously administered 30 minutes before the PTH injection.

The results for each group were expressed in terms of mean±S.E. (standard error) and comparison was made among the groups by testing by one-way analysis of variance. The significance level was taken at 5%.

RESULTS:

The results obtained by the subcutaneous administration and the oral administration are shown in Table 1 and Table 2, respectively.

TABLE 1 (1)

| | Subcutaneous administration (Administered 24 hours before the PTH injection) | | |
|---|---|---|---|
| Compound Tested | Dose (/kg) | N | Serum $Ca^{++}$ (m mole/liter) |
| Normal Control | — | 5 | 1.40 ± 0.01** |
| Control | — | 5 | 1.56 ± 0.01 |
| Compound of Example 12 | 30 mg | 5 | 1.44 ± 0.02** |
| Compound of Example 14 | 30 mg | 5 | 1.45 ± 0.02** |
| Normal Control | — | 5 | 1.38 ± 0.01** |
| Control | — | 5 | 1.49 ± 0.00 |
| SCT | 0.3 IU | 5 | 1.07 ± 0.02** |
| Compound of Manufacture Example 1 | 0.3 mg | 5 | 1.43 ± 0.02** |
| | 1.0 mg | 5 | 1.40 ± 0.01** |
| | 3.0 mg | 5 | 1.36 ± 0.02** |
| Normal Control | — | 5 | 1.40 ± 0.01** |
| Control | — | 5 | 1.52 ± 0.01 |
| Compound of Manufacture Example 2 | 30 mg | 5 | 1.41 ± 0.02** |

Mean value ± S.E.
**P <0.01

TABLE 1 (2)

| | Subcutaneous administration (Administered 72 hours before the PTH injection) | | |
|---|---|---|---|
| Compound Tested | Dose (/kg) | N | Serum $Ca^{++}$ (m mole/liter) |
| Normal Control | — | 5 | 1.41 ± 0.01** |
| Control | — | 5 | 1.52 ± 0.00 |
| Compound of Example 6 | 0.1 mg | 5 | 1.42 ± 0.02** |
| | 0.3 mg | 5 | 1.25 ± 0.02** |
| Compound of Example 8 | 0.1 mg | 5 | 1.41 ± 0.02** |
| | 0.3 mg | 5 | 1.27 ± 0.02** |
| Normal Control | — | 5 | 1.41 ± 0.01** |
| Control | — | 5 | 1.50 ± 0.02 |
| Compound of Example 21 | 0.01 mg | 5 | 1.47 ± 0.02 |
| | 0.03 mg | 5 | 1.38 ± 0.01** |

TABLE 1 (2)-continued

| | Subcutaneous administration (Administered 72 hours before the PTH injection) | | |
|---|---|---|---|
| Compound Tested | Dose (/kg) | N | Serum $Ca^{++}$ (m mole/liter) |
| | 0.10 mg | 5 | 1.22 ± 0.003** |
| Normal Control | — | 5 | 1.41 ± 0.02** |
| Control | — | 5 | 1.46 ± 0.02 |
| Compound of Example 22 | 0.01 mg | 5 | 1.45 ± 0.01 |
| | 0.03 mg | 5 | 1.35 ± 0.01** |
| | 0.10 mg | 5 | 1.21 ± 0.02** |
| Normal Control | — | 5 | 1.43 ± 0.00 |
| Control | — | 5 | 1.48 ± 0.02 |
| Compound of Example 23 | 0.03 mg | 5 | 1.40 ± 0.01** |
| | 0.1 mg | 5 | 1.33 ± 0.01** |
| Normal Control | — | 5 | 1.34 ± 0.02** |
| Control | — | 5 | 1.43 ± 0.01 |
| Compound of Example 25 | 0.1 mg | 5 | 1.39 ± 0.02** |
| | 0.3 mg | 5 | 1.22 ± 0.01** |
| Normal Conrtrol | — | 5 | 1.35 ± 0.02** |
| Control | — | 5 | 1.44 ± 0.01 |
| Compound of Example 25 | 0.3 mg | 5 | 1.43 ± 0.03 |
| | 1.0 mg | 5 | 1.36 ± 0.02* |
| Normal Control | — | 5 | 1.47 ± 0.02** |
| Control | — | 5 | 1.57 ± 0.02 |
| Compound of Example 28 | 0.1 mg | 5 | 1.36 ± 0.01** |
| | 0.3 mg | 5 | 1.18 ± 0.02** |
| Known Compound (note-1) | 1.0 mg | 5 | 1.43 ± 0.02** |
| Normal Control | — | 5 | 1.35 ± 0.02** |
| Control | — | 5 | 1.44 ± 0.01 |
| Compound of Example 31 | 0.1 mg | 5 | 1.20 ± 0.01** |
| | 0.3 mg | 5 | 1.05 ± 0.03** |
| Normal Control | — | 5 | 1.36 ± 0.01* |
| Control | — | 5 | 1.45 ± 0.01 |
| Compound of Example 32 | 0.1 mg | 5 | 1.41 ± 0.02 |
| | 0.3 mg | 5 | 1.27 ± 0.02** |
| Normal Control | — | 5 | 1.38 ± 0.01** |
| Control | — | 5 | 1.48 ± 0.02 |
| Etidronate | 10 mg | 5 | 1.44 ± 0.01 |
| | 30 mg | 5 | 1.40 ± 0.01** |
| Compound of Example 1 | 0.03 mg | 5 | 1.42 ± 0.02 |
| | 0.1 mg | 5 | 1.33 ± 0.01** |
| Control | — | 5 | 1.51 ± 0.03 |
| Compound of Manufacture Example 2 | 0.1 mg | 5 | 1.39 ± 0.02** |
| | 0.3 mg | 5 | 1.22 ± 0.02** |
| Normal Control | — | 5 | 1.42 ± 0.02* |
| Control | — | 5 | 1.54 ± 0.02 |
| Compound of Manufacture Example 3 | 0.3 mg | 5 | 1.45 ± 0.01 |
| | 1.0 mg | 5 | 1.23 ± 0.05** |
| Normal Control | — | 5 | 1.47 ± 0.02** |
| Control | — | 5 | 1.57 ± 0.02 |
| Known Compound (note-2) | 0.1 mg | 5 | 1.58 ± 0.00 |
| | 0.3 mg | 5 | 1.49 ± 0.01* |
| | 1.0 mg | 5 | 1.39 ± 0.02** |
| Known Compound (note-1) | 0.3 mg | 5 | 1.51 ± 0.03 |
| | 1.0 mg | 5 | 1.43 ± 0.02** |

Mean value ± S.E.
*P <0.05,
**: P <0.01
(Note-1): [(5-t-butyl-3-isoxazolyl)amino]methylene-bis(phosphonic acid) (disclosed in Japanese Patent Application (OPI) No. 89293/80)
(Note-2): [(5-isopropyl-3-isoxazolyl)amino]methylene-bis(phosphonic acid) (disclosed in Japanese Patent Application (OPI) No. 89293/80)

TABLE 2 (1)

| | Oral Administration (Administered 24 hours before the PTH injection) | | |
|---|---|---|---|
| Compound Tested | Dose (mg/kg) | N | Serum $Ca^{++}$ (m mole/liter) |
| Normal Control | — | 5 | 1.45 ± 0.01* |
| Control | — | 5 | 1.52 ± 0.02 |
| Compound of Manufacture Example 1 | 100 mg | 5 | 1.44 ± 0.02* |
| | 300 mg | 5 | 1.41 ± 0.01** |

Mean value ± S.E. *P <0.05, **P.<0.01

TABLE 2(2)

| Oral Administration | | | (Administered 72 hours before the PTH injection) |
|---|---|---|---|
| Compound Tested | Dose (mg/kg) | N | Serum $Ca^{++}$ (m mole/liter) |
| Normal Control | — | 5 | 1.40 ± 0.01** |
| Control | — | 5 | 1.52 ± 0.02 |
| Compound of | 30 mg | 5 | 1.48 ± 0.02 |
| Example 8 | 100 mg | 5 | 1.35 ± 0.02** |
| Normal Control | — | 5 | 1.42 ± 0.02* |
| Control | — | 5 | 1.54 ± 0.02 |
| Compound of | 10 mg | 5 | 1.52 ± 0.02 |
| Example 21 | 30 mg | 5 | 1.36 ± 0.06** |
|  | 100 mg | 5 | 1.33 ± 0.04** |
| Normal Control | — | 5 | 1.43 ± 0.00 |
| Control | — | 5 | 1.48 ± 0.02 |
| Compound of | 30 mg | 5 | 1.49 ± 0.00 |
| Example 23 | 100 mg | 5 | 1.41 ± 0.02** |
| Normal Control | — | 5 | 1.40 ± 0.01* |
| Control | — | 5 | 1.49 ± 0.01 |
| Compound of | 30 mg | 5 | 1.44 ± 0.02 |
| Example 22 | 100 mg | 5 | 1.28 ± 0.04** |
| Compound of | 30 mg | 5 | 1.46 ± 0.02 |
| Example 28 | 100 mg | 5 | 1.31 ± 0.04** |
| Normal Control | — | 5 | 1.46 ± 0.01 |
| Control | — | 5 | 1.52 ± 0.02 |
| Compound of | 30 mg | 5 | 1.48 ± 0.01 |
| Manufacture Example 1 | 100 mg | 5 | 1.16 ± 0.03** |
| Normal Control | — | 5 | 1.41 ± 0.02* |
| Control | — | 5 | 1.55 ± 0.01 |
| Compound of | 30 mg | 5 | 1.46 ± 0.02 |
| Manufacture Example 2 | 100 mg | 5 | 1.16 ± 0.07** |

Mean value ± S.E. *P <0.05, **P <0.01

(2) EFFECT FOR INHIBITION OF BONE RESORPTION:

A left forelimb of a rat was immobilized by cutting the brachial nerve of the left forelimb. The inhibitory effect of the compound on the immobilization-induced atrophy of bone was demonstrated as mentioned below.

TEST METHOD:

Five-week Wistar rats were used for the experiment. The atrophy of bone was induced by reference to A. D. Kenny's report (Calcif, Tissue Int., 37, 126-133, 1985). Specifically, the plexus brachialis of the left forelimb of the animal (rat) was cut under thiopental anesthesia so that the left forelimb was immobilized. No treatment was imparted to the right forelimb (for control). Rats of a pseudooperation group were treated in the same manner as above except that the plexus brachialis was not cut. After two weeks, both the left and right humeri were collected. The soft connective tissue was removed off from the humeri, the humeri were fully fixed dehydrated and defatted with ethanol, and the dry weight of the respective humeri was measured. Afterwards, these were fired at 800° C. for 24 hours and the ashed weight was measured.

The compound was prepared in the same manner as in the above-mentioned Test Method (1) and was subcutaneously administered once a day for 14 days from the day of the operation, in the same manner as in the Test Method (1). For the control group and the pseudooperation group, only a physiological saline was injected in the same manner.

The results for each group were expressed in terms of means ±S.E. (standard error) and comparison was made among the groups by testing one-way analysis of variance. The significance level was taken at 5%.

RESULTS:

TABLE 3

|  | Dose (mg/kg) | N | Difference of Bone Weight (mg) (a) | Difference of Bone Ash Content (mg) (b) |
|---|---|---|---|---|
| Pseudooperation Group | — | 5 | −0.4 ± 0.4** | −0.4 ± 0.3** |
| Control Group | — | 5 | 21.8 ± 2.2 | 14.7 ± 0.7 |
| Compound of | 3 | 4 | 8.0 ± 1.0** | 4.8 ± 0.5** |
| Manufacture Example 1 | 10 | 5 | 3.2 ± 0.7** | 1.7 ± 0.5** |
| Pseudooperation Group | — | 5 | 1.1 ± 3.0 | 0.4 ± 0.8 |
| Control Group | — | 5 | 13.6 ± 1.3 | 9.6 ± 0.9 |
| Compound of Manufacture Example 2 | 1.0 | 5 | 4.8 ± 1.3** | 3.0 ± 0.7** |

Effect on Disuse Atrophy of Bone induced by Neurectomy in Rats

| | | | Left humerus | | |
|---|---|---|---|---|---|
| Compound Tested | Dose (mg/kg) | N | Dry weight (mg) | Ashed weight (mg) | Ashed weight Dry weight % |
| | | | Subcutaneous Administration (2 weeks) | | |
| Pseudooperation Group | — | 5 | 120.6 ± 2.7** | 66.6 ± 1.5 | 55.2 ± 0.1** |
| Control Group | — | 5 | 96.6 ± 2.8 | 51.3 ± 1.4 | 55.3 ± 0.1 |
| Compound of Example 21 | 0.01 | 5 | 116.5 ± 1.5** | 65.7 ± 0.9** | 56.4 ± 0.2** |
| | 0.03 | 5 | 129.2 ± 1.0** | 73.6 ± 0.7** | 56.9 ± 0.2** |
| | 0.1 | 5 | 130.1 ± 3.2** | 72.8 ± 1.8** | 55.9 ± 0.4** |
| Pseudooperation Group | — | 5 | 109.8 ± 2.6** | 61.6 ± 1.6** | 56.1 ± 0.3** |
| Control Group | — | 5 | 97.3 ± 2.4 | 52.9 ± 1.6 | 54.4 ± 0.5 |
| Compound of Manufacture | 0.1 | 5 | 113.9 ± 2.0** | 64.9 ± 1.2** | 56.9 ± 0.1** |
| | 0.3 | 5 | 114.4 ± 2.6** | 65.4 ± 1.6** | 57.2 ± 0.3** |

TABLE 3-continued

| | | | | | |
|---|---|---|---|---|---|
| Example 1 | 1.0 | 5 | 121.3 ± 2.1** | 70.1 ± 1.1** | 57.8 ± 0.4** |
| | Oral Administration | | | | |
| | (2 weeks) | | | | |
| Pseudooperation Group | — | 5 | 120.6 ± 2.7 | 66.6 ± 1.5** | 55.2 ± 0.1** |
| Control Group | — | 5 | 96.6 ± 2.8 | 51.3 ± 1.4 | 55.3 ± 0.1 |
| Compound of Example 21 | 3 | 5 | 113.0 ± 3.1 | 64.4 ± 2.3** | 54.4 ± 0.2** |
| | 10 | 5 | 115.2 ± 4.0 | 67.0 ± 1.2** | 56.0 ± 0.4** |
| | 30 | 5 | 118.7 ± 2.0 | 65.7 ± 0.9** | 56.5 ± 0.2** |
| Pseudooperation Group | — | 5 | 120.5 ± 2.1** | 64.7 ± 1.0** | 53.7 ± 0.2** |
| Control Group | — | 5 | 106.0 ± 1.9 | 54.8 ± 1.0 | 51.6 ± 0.4 |
| Compound of Manufacture Example 1 | 10 | 5 | 102.8 ± 2.2 | 54.9 ± 1.3 | 53.4 ± 0.3** |
| | 30 | 5 | 112.1 ± 1.4 | 61.0 ± 1.0** | 54.4 ± 0.3** |
| | 100 | 5 | 123.9 ± 2.3** | 68.9 ± 1.3** | 55.6 ± 0.2** |

Note:
Mean value ± S.E.
**$P < 0.01$
(a): (dry weight of non-treated humerus) − (dry weight of treated humerus)
(b): (ashed weight of non-treated humerus) − (ashed weight of treated humerus)

(3) ANTARTHRITIC EFFECT:

The excellent prophylactic and therapeutic action of the compounds (I) of the present invention against arthritis was demonstrated and confirmed by the following test methods.

Specifically, for investigation of the anti-arthritic effect, experimental models of adjuvant arthritis which is resemble to rheumatoid arthritis in human were used in two test methods. In one method to test the therapeutic effect of the compounds, the compounds to be tested were administered to the animals already having the adjuvant arthritis. In the other method to test the prophylactic effect of the compounds, these were administered after the adjuvant administration, and the expression and progress of the resulting arthritis, if any, was observed.

The two tests for the therapeutic and the prophylactic effect are mentioned in detail hereunder.

EXPERIMENT (3)-I:

Therapeutic Effect on Adjuvant Arthritis in Rats.

0.1 ml of a suspension of dry dead cells of *Mycobacterium butyricum* as suspended in liquid paraffin in a proportion of 6 mg/ml was subcutaneously injected to male Lewis rats (7-week) in the tail. After 17 or 18 days, the thickness of the both hind paws was measured. One group comprising six rats in which the arthritis was noticeably observed was isolated. After the grouping day, the compound to be tested was subcutaneously or orally administered once a day for 14 days to the rats. Next day after the last administration, the thickness of the soles of the both hind legs was again measured.

EXPERIMENT (3)-II:

Prophylactic Effect on Adjuvant Arthritis in Rats.

0.05 ml of the suspension of dry dead bacilli of *Mycobacterium butyricum* as suspended in liquid paraffin in a proportion of 6 mg/ml was subcutaneously injected to male Lewis rats (6 to 7-week) in the left hind paw. After the adjuvant injection, the compound to be tested was administered to the rats once a day for 21 days. Next day after the last administration, the thickness of the both hind paws of the rats was measured.

For the Experiments (3)-I and (3)-II, the compounds of the present invention were dissolved, using sodium hydroxide and hydrochloric acid in physiological saline (pH 7.4), for subcutaneous administration, in such amount that the dose amounted to 2 ml/kg, and for oral administration, in distilled water (pH 7.4) so that the dose amounted to 5 ml/kg; and indometacin (as comparative drug) was suspended in 0.5% methyl cellulose solution so that the dose amounted to 5 ml/kg. Each rat was weighed at the first day of starting the administration of the compound to be tested and at the last day of the administration of the compound, and the difference of the weight there between (ΔB.W.) was obtained.

The results for each group were expressed in terms of mean ±S.E. (standard error) and comparison was made among the groups by testing by one-way analysis of variance. The significance level was taken at 5%.

TABLE 4

Experiment (3)-I

Subcutaneous Administration

| | Dose (mg/kg) | Administration Route | N | ΔB.W. (g) | Thickness of Paw (average of right and left paws) (× 0.01 mm) |
|---|---|---|---|---|---|
| Normal Control (physiological salt solution) | — | sc | 6 | 57 ± 3** | 658 ± 1** |
| Arthritic Control (physiological salt solution) | — | sc | 6 | 32 ± 1 | 1401 ± 32 |
| Indometacin | 1 | po | 6 | 67 ± 4** | 956 ± 32** |
| Compound of Manufacture Example 1 | 0.1 | sc | 6 | 40 ± 2 | 1258 ± 31** |
| | 0.3 | sc | 6 | 50 ± 2** | 1102 ± 36** |
| | 1.0 | sc | 6 | 56 ± 4** | 956 ± 36** |
| | 3.0 | sc | 6 | 56 ± 1** | 974 ± 32** |

TABLE 5

Experiment (3)-I
Oral Administration

| | Dose (mg/kg) | Administration Route | N | ΔB.W. (g) | Thickness of Paw (average of right and left paws) (× 0.01 mm) |
|---|---|---|---|---|---|
| Normal Control (physiological salt solution) | — | po | 6 | 41 ± 4 | 736 ± 5** |
| Arthritic Control (physiological salt solution) | — | po | 6 | 21 ± 2 | 1460 ± 32 |
| Indometacin | 1 | po | 6 | 51 ± 4** | 1044 ± 46** |
| Compound of Manufacture Example 1 | 100 | po | 6 | 50 ± 3** | 1131 ± 36** |
| Normal Control (physiological salt solution) | — | po | 6 | 51.5 ± 3.3** | 747 ± 2** |
| Arthritic Control (physiological salt solution) | — | po | 6 | 24.2 ± 1.3 | 1435 ± 48 |
| Indometacin | 1 | po | 6 | 58.2 ± 1.9** | 931 ± 26** |
| Compound of Example 21 | 10 | po | 6 | 29.7 ± 1.1 | 1317 ± 35 |
| | 30 | po | 6 | 30.0 ± 1.1 | 1321 ± 35 |
| | 100 | po | 6 | 29.7 ± 4.5 | 1119 ± 52** |
| Compound of Manufacture Example 1 | 10 | po | 6 | 23.3 ± 0.9 | 1435 ± 49 |
| | 30 | po | 6 | 32.8 ± 1.7 | 1296 ± 45* |
| | 100 | po | 6 | 43.3 ± 2.0** | 1083 ± 36** |

TABLE 6

Experiment (3) II
Subcutaneous Administration

| | Dose (mg/kg) | Administration Route | N | ΔB.W. (g) | Thickness of Paw (× 0.01 mm) Left | Thickness of Paw (× 0.01 mm) Right |
|---|---|---|---|---|---|---|
| Arthritic Control (physiological salt solution) | — | sc | 6 | 230 ± 4 | 1451 ± 2.8 | 1298 ± 33 |
| Indometacin | 1 | po | 6 | 261 ± 7* | 1096 ± 41** | 1028 ± 47** |
| Compound of Manufacture Example 1 | 0.1 | sc | 6 | 238 ± 2 | 1277 ± 19** | 1279 ± 27 |
| | 0.3 | sc | 6 | 239 ± 2 | 1158 ± 12** | 1107 ± 25** |
| | 1.0 | sc | 6 | 233 ± 3 | 1174 ± 14** | 1110 ± 28** |

*$P < 0.05$,
**$P < 0.01$

The above-mentioned experimental results apparently demonstrate that the compound of the present invention had an inhibitory effect at least against to 0.01 mg/kg paw swelling by subcutaneous administration in the remedial experiment (Experiment (3)-I) and the $ED_{50}$ value of the said compound was 0.57 mg/kg. By oral administration, the said compound was also effective in an amount of 100 mg/kg. Further, in the prophylactic experiment (Experiment (3)-II), the compound was also confirmed to be effective by subcutaneous administration. Specifically, this had a significant inhibitory effect in the adjuvant-inoculated paw by subcutaneous administration of 0.1 mg/kg and in the opposite paw with no adjuvant by injection of 0.3 mg/kg.

(4) ACUTE TOXICITY TEXT:

The compound of Manufacture Example 1 was subcutaneously injected to rats in an amount of 10 mg/kg/day for continuous two weeks, and no rats died.

The compounds (I) of the present invention can be blended with any optional pharmaceutically acceptable carrier, vehicle, attenuant, etc. to be formed into powder, granules, tablets, capsules, pills, etc. for oral administration or into injection (for intro-articular injection, etc.), suppositories, inhalation, ointment, etc. for non-peroral administration. The amount of the dose of the compounds (I) of the present invention is, although varying in accordance with the administration route, patient's symptom, etc., generally form 10 mg/day/adult to 1 g/day/adult, preferably from 10 to 100 mg/day/adult, for oral administration, and from 0.1 to 100 mg/day/adult for non-oral administration.

DESCRIPTION OF THE PREFERRED EMBODIMENTS

The following examples are intended to illustrate the present invention in more detail but not to limit it in any way. Manufacture of the raw material compound to be used in Examples is shown in Referential Example. Some of the raw material compounds were prepared in accordance with the methods described in "Industrial Chemistry" 66 (12), 1831 (1963) (S. Kishimoto) and Japanese Patent Publication No. 4887/62 (H. Kano et al.).

Manufacture of the known compounds included in the scope of the compounds (I) of the present invention is shown in Manufacture Examples.

REFERENCE EXAMPLE 1:

Raw Material Compound for Example 15

4.7 g of sodium metal was dissolved in 92 ml of ethanol. A mixture of 20 g of 2-heptanone and 26 g of diethyl oxalate was dropwise added thereto at 0° C. After the removing the ice bath, the reaction mixture was stirred at room temperature for 3 hours. After evaporation of the reaction mixture, 200 ml of water was added to the resulting syrup, and then an aqueous 10% hydrochloric acid was added with ice-cooling, the pH being adjusted to 1. After extraction with benzene (300 ml×3), the organic layer was washed with 100 ml of water, dried with Glauber's salt ($Na_2SO_4$). And concentrated to give ethyl hexanoylpyruvate as a liquid (38 g).

A mixture of 38 g of ethyl hexanoylpyruvate in 190 ml of ethanol in the presence of 14.4 g of hydroxylamine hydrochloride and 16 g of sodium hydrogencarbonate was heated under reflux for 3 hours. After the reaction mixture was cooled to room temperature, the insoluble materials were separated by filtration, and the remaining filtrate was concentrated. The resulting residue was dissolved in chloroform (500 ml), which was washed with water, concentrated to give 5-pentyl-3-carboethoxyisoxazole as a liquid (36 g).

A mixture of 36 g of 5-pentyl-3-carboethoxyisoxazole in 105 ml of a concentrated aqueous ammonia was vigorously stirred overnight. The reaction mixture was filtered, and the resulting solid was washed with water and dried to obtain 20 g of 5-pentyl-3-carbamidoisoxazole.

Subsequently, 19 g of the thus obtained 3-carbamide was added to a solution of 77.5 ml of an aqueous 10% sodium hypochlorite containing 8.3 g of sodium hydroxide. The mixture was stirred for 2 hours at room temperature. The reaction mixture was dropped into 60 ml of a boiling water for 40 minutes, and then refluxed for further 40 minutes. The reaction mixture was rapidly cooled to give crystals. The crystals thus formed were filtered and washed with water to obtain 10 g of 3-amino-5-pentylisoxazole.

EXAMPLE 1:

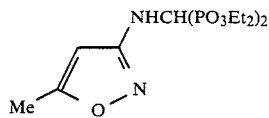

A mixture of 4.9 g of 3-amino-5-methylisoxazole, 8.8 g of ethyl ortho-formate and 13.8 g of diethyl phosphite was heated at 150° C. with stirring for 40 minutes. The reaction mixture was cooled to room temperature and the product was purified on silica-gel column (eluent: 2% methanol-chloroform) to give 4.8 g of tetraethyl [(5-methyl-3-isoxazolyl)amino]methylene-bis(phosphonate) as an oil.

The physico-chemical characteristics of this product are as follows:

(i) Mass Spectrum (FAB Mass): 385 (M+1)
(ii) Nuclear Magnetic Resonance (NMR) Spectrum: (in $CDCl_3$)

| δ: | 1.3 | (12H, | $CH_3CH_2O \times 4$) |
|---|---|---|---|
|  | 2.3 | (3H, | $CH_3$) |
|  | 4.0~4.4 | (8H, | $CH_3CH_2O \times 4$) |
|  | 4.52 | (1H, | NHCH—) |
|  | 5.60 | (1H, | H in isoxazole ring) |

EXAMPLE 2:

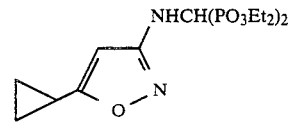

A mixture of 2.0 g of 3-amino-5-cyclopropyl-isoxazole, 3.0 g of ethyl ortho-formate and 9.1 g of diethyl phosphite was heated at 160° C. with stirring for 2.5 hours. The reaction mixture was cooled to room temperature and the product was purified on a silica gel column (eluent: 2% methanol-chloroform) to give 2.5 g of tetraethyl [(5-cyclopropyl-3-isoxazolyl)-amino]-methylene-bis(phosphonate) as an oil.

The physico-chemical characteristics of this product are as follows:

(i) Pale Yellow Oil (at room temperature)
(ii) Mass Spectrum (FAB Mass): 411 (M+1), 365, 273
(iii) NMR Spectrum (in $CDCl_3$):

| δ: | 0.84~1.10 | (4H, —CH<$\genfrac{}{}{0pt}{}{CH_2}{CH_2}$) |
|---|---|---|
|  | 1.34 | (12H, —$OCH_2CH_3$) |
|  | 1.92 | (12H, —C$\underline{H}$<$\genfrac{}{}{0pt}{}{CH_2}{CH_2}$) |
|  | 2.04 | (1H, N$\underline{H}$) |
|  | 4.04~4.40 | (8H, —OC$\underline{H}_2$$CH_3$) |
|  | 4.48 | (1H, —NHC$\underline{H}$—) |
|  | 5.48 | (1H, $\underline{H}$——NH—, isoxazole ring) |

In the same manner as Example 2, the following compounds were prepared.

EXAMPLE 3:

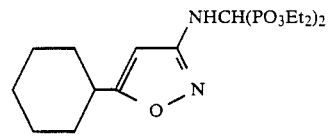

Tetraethyl [(5-cyclohexyl-3-isoxazolyl)amino]methylene-bis(phosphonate)

(i) Yellow Oil
(ii) Mass Spectrum (FAB Mass): 453 (M+1), 407, 315
(iii) NMR Spectrum (in $CDCl_3$):

| δ: | 1.30 | (12H, —$OCH_2C\underline{H}_3$) |
|---|---|---|

-continued

| | | |
|---|---|---|
| 1.20~2.20 | 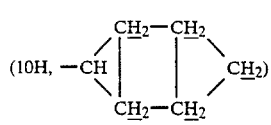 | (10H, —CH, CH₂—CH₂, CH₂—CH₂, CH₂) |
| 1.84 | | (1H, —NHCH—) |
| 2.64 | 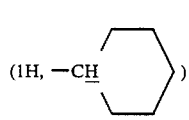 | (1H, —CH⟨⟩) |
| 4.04~4.46 | | (8H, —OCH₂CH₃) |
| 4.50 | | (1H, —NHCH—) |
| 5.50 | 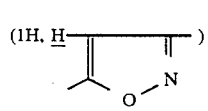 | (1H, H—) |

Starting Compound: 3-Amino-5-cyclohexylisoxazole

EXAMPLE 4:

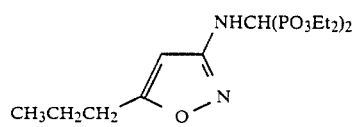

Tetraethyl [(5-propyl-3-isoxazolyl)amino]methylene-bis(phosphonate)

(i) Yellow Oil
(ii) Mass Spectrum (FAB Mass): 413 (M+1), 367, 275
(iii) NMR Spectrum (in CDCl₃):

| δ: | 0.96 | (3H, —CH₂CH₂CH₃) |
|---|---|---|
| | 1.30 | (12H, —OCH₂CH₃) |
| | 1.68 | (2H, —CH₂CH₂CH₃) |
| | 1.76 | (1H, —NHCH) |
| | 2.59 | (2H, CH₂CH₂CH₃) |
| | 4.02~4.46 | (8H, —OCH₂CH₃) |
| | 4.48 | (1H, —NHCH—) |
| | 5.54 | (1H, H—) 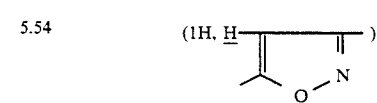 |

Starting Compound 3-Amino-5-n-propylisoxazole

EXAMPLE 5:

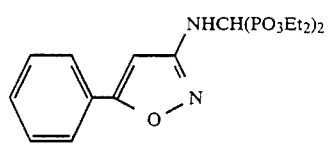

Tetraethyl [(5-phenyl-3-isoxazolyl)amino]methylene-bis(phosphonate)

(i) Yellow Oil
(ii) Mass Spectrum (FAB Mass): 447 (M+1), 401, 309
(iii) NMR Spectrum (in CDCl₃):

| δ: | 1.30 | (12H, —OCH₂CH₃) |
|---|---|---|
| | 4.06~4.44 | (8H, —OCH₂CH₃) |
| | 4.62 | (1H, —NHCH—) |
| | 6.10 | (1H, H—) 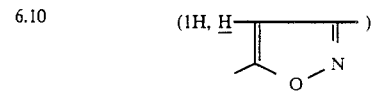 |
| | 7.34~7.82 | (5H, —) 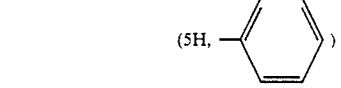 |

Starting Compound: 3-Amino-5-phenylisoxazole

EXAMPLE 6:

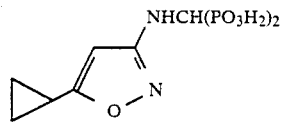

A solution of 2.5 g of tetraethyl [(5-cyclopropyl-3-isoxazolyl)-amino]methylene-bis(phosphonate) in 25 ml of concentrated hydrochloric acid was heated under reflux for 3.5 hours. The reaction mixture was concentrated. Methanol and acetone were added to the concentrate to give 1.7 g of [(5-cyclopropyl-3-isoxazolyl)-amino]-methylene-bis(phosphonic acid) as a solid.

(i) m.p.: 176°-178° C.
(ii) Mass Spectrum (FAB Mass): 299 (M+1), 217
(iii) NMR Spectrum (in D₂O):

| δ: | 0.80~1.16 | (4H, —CH⟨CH₂/CH₂⟩) 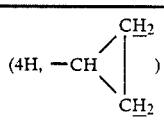 |
|---|---|---|
| | 1.84~2.12 | (1H, —CH⟨CH₂/CH₂⟩) 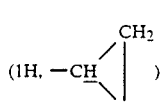 |
| | 4.08 | (1H, —NHCH—) |

| 5.82 | (1H, 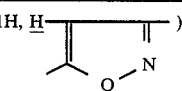) |

(iv) Elementary Analysis (as $C_7H_{12}N_2O_7P_2 \cdot 0.5H_2O$):

|  | C(%) | H(%) | N(%) | P(%) |
| --- | --- | --- | --- | --- |
| Calculated: | 27.37 | 4.27 | 9.12 | 20.17 |
| Found: | 27.14 | 4.02 | 9.05 | 20.09 |

In the same manner as Example 6, the following compounds were prepared.

EXAMPLE 7:

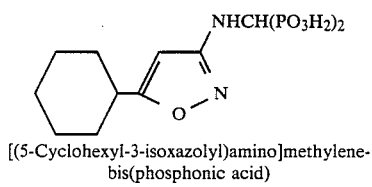

[(5-Cyclohexyl-3-isoxazolyl)amino]methylene-bis(phosphonic acid)

(i) m.p.: 208°–209° C.
(ii) Mass Spectrum (FAB Mass): 341 (M+1), 259, 177
(iii) NMR Spectrum (in $D_2O$):

| δ: | 1.20~2.12 | 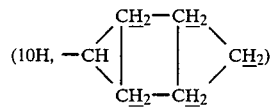 |
| | | (10H, —CH ) |
| | 2.68 | 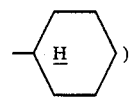 |
| | | (  ) |
| | 4.06 | (1H, —NCH—) |
| | 5.86 | (1H, 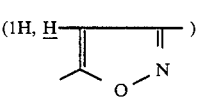 ) |

(iv) Elementary Analysis (as $C_{10}H_{18}N_2O_7P_2 \cdot 0.3H_2O$):

|  | C(%) | H(%) | N(%) | P(%) |
| --- | --- | --- | --- | --- |
| Calculated: | 34.74 | 5.42 | 8.11 | 17.92 |
| Found: | 34.65 | 5.14 | 8.15 | 18.06 |

EXAMPLE 8:

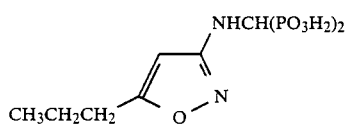

[(5-n-Propyl-3-isoxazolyl)amino]methylene-bis(phosphonic acid)

(i) m.p.: 152°–153° C.

(ii) Mass Spectrum (FAB Mass): 301 (M+1), 219
(iii) NMR Spectrum (in $D_2O$):

| δ: | 0.92 | (3H, —CH$_2$CH$_2$CH$_3$) |
| | 1.66 | (2H, —CH$_2$CH$_2$CH$_3$) |
| | 2.62 | (2H, CH$_2$CH$_2$CH$_3$) |
| | 4.12 | (1H, —NHCH—) |
| | 5.90 | (1H, 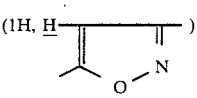 ) |

(iv) Elementary Analysis (as $C_7H_{14}N_2O_7P_2 \cdot 0.4H_2O$):

|  | C(%) | H(%) | N(%) | P(%) |
| --- | --- | --- | --- | --- |
| Calculated: | 27.36 | 4.85 | 9.11 | 20.16 |
| Found: | 27.34 | 4.55 | 9.13 | 20.39 |

EXAMPLE 9:

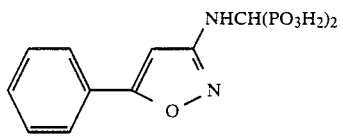

[(5-Phenyl-3-isoxazolyl)amino]methylene-bis(phosphonic acid)

(i) m.p.: 237°–238° C. (decomposition)
(ii) Mass Spectrum (FAB Mass): 335 (M+1), 253
(iii) NMR Spectrum (in $D_2O$ with $K_2CO_3$):

| δ: | 3.96 | (1H, —NHCH—) |
| | 6.44 | (1H, 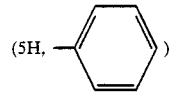 ) |
| | 7.44~7.90 | (5H, ) |

(iv) Elementary Analysis (as $C_{10}H_{12}N_2O_7P_2$):

|  | C(%) | H(%) | N(%) | P(%) |
| --- | --- | --- | --- | --- |
| Calculated: | 35.94 | 3.62 | 8.38 | 18.54 |
| Found: | 36.09 | 3.79 | 8.12 | 18.85 |

EXAMPLE 10:

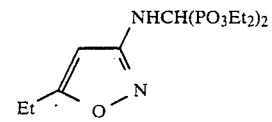

A mixture of 2.2 g of 3-amino-5-ethylisoxazole, 3.4 g of ethyl ortho-formate and 8.1 g of diethyl phosphite was heated at 150°–155° C. with stirring for 45 minutes. The reaction mixture was concentrated under reduced pressure, and the resulting residue was purified on a silica gel column (eluent: 0.5–2% methanolchloroform) to give 5.7 g of [(5-ethyl-3-isoxazolyl)amino]methylene-bis(phosphonate) as an oil.

The physico-chemical characteristics of this product are as follows:
(i) Mass Spectrum (FAB Mass): 399 (M+1)
(ii) NMR Spectrum (in CDCl₃):

| δ: | 1.1 ~ 1.5 | (15H, | —OCH₂CH₃ × 4, | —CH₂CH₃) |
|---|---|---|---|---|
| | 2.64 | (2H, | —CH₂CH₃) | |
| | 4.0 ~ 4.4 | (8H, | —OCH₂CH₃ × 4) | |
| | 4.50 | (1H, | —NHCH—) | |
| | 5.56 | (1H, | H in isoxazole ring) | |

EXAMPLE 11:

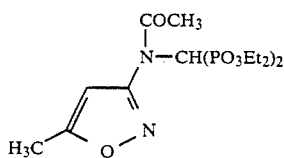

6 g of tetraethyl [(5-methyl-3-isoxazolyl)amino]methylene-bis(phosphonate) was dissolved in 60 ml of acetic anhydride and heated under reflux overnight. The reaction solution was concentrated under reduced pressure, and the resulting syrup was formed into a chloroform solution. This was washed with water and dried, and then the solvent was removed by distillation. The residue was purified on a silica gel column (eluent: 0.5–2% ethanolchloroform) to give 5.2 g of tetraethyl [N-acetyl(5-methyl-3-isoxazolyl)amino]methylene-bis(phosphonate) as a pale yellow syrup.

This had the following physico-chemical property.
(i) Mass Spectrum (FAB Mass): 427 (M+1)
(ii) NMR Spectrum (in CDCl₃):

| δ: | 1.32 | (12H, | —OCH₂CH₃ × 4) |
|---|---|---|---|
| | 2.12 | (3H, | —NCOCH₃) |
| | 2.46 | (3H, | —CH₃) |
| | 4.0 ~ 4.4 | (8H, | —OCH₂CH₃ × 4) |
| | 6.06 | (1H, | —NCH) |
| | 6.56 | (1H, | H in isoxazole ring) |

EXAMPLE 12:

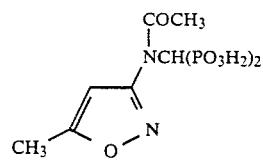

Iodotrimethylsilane (2.68 ml) was added to an ice-cooled solution of 2 g of tetraethyl [N-acetyl(5-methyl-3-isoxazolyl)amino]methylene-bis(phosphonate) in 20 ml of carbon tetrachloride. Then the temperature was allowed to rise to room temperature, and the mixture was stirred for 1 hour. The reaction mixture was concentrated, methanol was then added, and the mixture was again concentrated. The residue thus obtained was washed with ether, hexane and acetone to give a solid which was recrystallized from acetone-hexane to give 0.5 g of [N-acetyl(5-methyl-3-isoxazolyl)amino]methylene-bis(phosphonic acid) as crystals.

The physico-chemical characteristics of this product are as follows:
(i) Elementary Analysis (as $C_7H_{12}N_2O_8P_2$):

| | C(%) | H(%) | N(%) |
|---|---|---|---|
| Calculated: | 26.77 | 3.85 | 8.92 |
| Found: | 26.98 | 3.84 | 8.72 |

(ii) Mass Spectrum (FAB Mass): 315 (M+1)
(iii) NMR Spectrum (in D₂O):

| δ: | 2.10 | (3H, | NCOCH₃) |
|---|---|---|---|
| | 2.48 | (3H, | —CH₃) |
| | 5.32 | (1H, | NCH) |
| | 6.50 | (1H, | H in isoxazole ring) |

EXAMPLE 13:

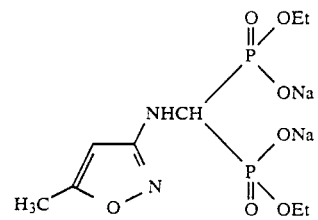

Iodotrimethylsilane (1.2 ml; 2 molar equivalents) was added dropwise to an ice-cooled solution of 1.6 g of tetraethyl [(5-methyl-3-isoxazolyl)amino]methylene-bis(phosphonate) in 16 ml of carbon tetrachloride. Then the temperature was allowed to rise to room temperature, and the mixture was stirred for 1 hour. The reaction mixture was concentrated, methanol was then added, and the mixture was again concentrated. The residue thus obtained was washed with hexane, and then dissolved in 0.1N aqueous sodium hydroxide, the pH being adjusted to 7. The solution was applied to an HP-20 resin column for purification (eluent: water) to give 0.2 g of disodium diethyl [(5-methyl-3-isoxazolyl)amino]methylene-bis(phosphonate) as a solid.

The physico-chemical characteristics of this product are as follows:
(i) Elementary Analysis (as $C_9H_{16}N_2Na_2O_7P_2 \cdot H_2O$):

| | C (%) | H (%) | N (%) |
|---|---|---|---|
| Calculated: | 27.71 | 4.65 | 7.18 |
| Found: | 27.67 | 4.32 | 7.22 |

(ii) Mass Spectrum (FAB Mass): 327 (M−1)
(iii) NMR Spectrum (in D₂O):

| δ: | 1.18 | (6H, —OCH₂C$\underline{H}$₃ × 2) |
|---|---|---|
| | 2.30 | (3H, —CH₃) |
| | 3.8~4.8 | (4H, —OC$\underline{H}$₂CH₃ × 2) |
| | 3.96 | (1H, —NHC$\underline{H}$—) |
| | 5.82 | (1H, H in isoxazole ring) |

EXAMPLE 14:

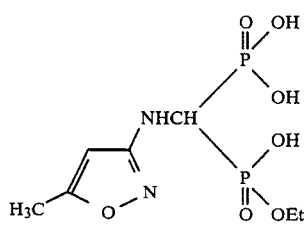

Iodotrimethylsilane (1.8 ml; 3 molar equivalents) was added dropwise to an ice-cold solution of 1.6 g of tetraethyl [(5-methyl-3-isoxazolyl)amino]methylene-bis(phosphonate) in 16 ml of carbon tetrachloride. Then the temperature was allowed to rise to room temperature, and the mixture was stirred for 1 hour. The reaction mixture was concentrated, methanol was then added, and the mixture was again concentrated. The residue thus obtained was washed with hexane, and dissolved in water. The solution was applied to an HP-20 resin column for purification (eluent: water) to give 0.27 g of ethyl [(5-methyl-3-isoxazolyl)amino]methylene-bis(phosphonate) as a solid.

The physico-chemical characteristics of this product are as follows:

This had the following physico-chemical property.
(i) Elementary Analysis (as $C_7H_{14}N_2O_7P_2 \cdot 0.5H_2O$):

|  | C(%) | H(%) | N(%) |
|---|---|---|---|
| Calculated: | 27.17 | 4.85 | 9.06 |
| Found: | 27.39 | 4.60 | 9.44 |

(ii) Mass Spectrum (FAB Mass): 301 (M+1)
(iii) NMR Spectrum (in $D_2O$):

| δ: | 1.22 | (3H, —OCH$_2$C$\underline{H}_3$) |
|---|---|---|
|  | 2.30 | (3H, —CH$_3$) |
|  | 3.8~4.2 | (2H, —OC$\underline{H}_2$CH$_3$) |
|  | 4.12 | (1H, —NHCH—) |
|  | 5.88 | (1H, H in isoxazole ring) |

EXAMPLE 15:

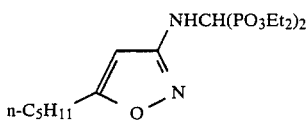

A mixture of 2 g of 3-amino-5-n-pentylisoxazole, 2.3 g of ethyl orthoformate and 7.2 g of diethyl phosphite was heated at 150° C. with stirring for 60 minutes. The reaction mixture was concentrated under reduced pressure, and the resulting residue was purified on a silicagel column (eluent: 0 to 3% methanol-chloroform) to give 3.2 g of tetraethyl [(5-n-pentyl-3-isoxazolyl)amino]-methylene-bis(phosphonate) as a pale yellow oil.

The physico-chemical characteristics of this product are as follows:

This had the following physico-chemical property.
(i) Mass Spectrum (FAB Mass): 441 (M+1)
(ii) NMR Spectrum (in CDCl$_3$):

| δ: | 0.9 | (3H, CH$_3$—) |
|---|---|---|
|  | 1.2~1.8 | (18H, —(CH$_2$)$_3$—, OCH$_2$C$\underline{H}_3$ × 4) |
|  | 2.6 | (2H, CH$_2$—⫞$_O$ ) |
|  | 4.0~4.4 | (8H, OC$\underline{H}_2$CH$_3$ × 4) |
|  | 4.5 | (1H, CH⟨$_P^P$ ) |
|  | 5.5 | (1H, H in isoxazole ring) |

In the same manner as Example 15, the following compounds were prepared.

EXAMPLE 16:

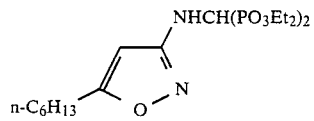

Tetraethyl [(5-n-hexyl-3-isoxazolyl)amino]methylene-bis(phosphonate)

Physico-chemical property:
(i) Mass Spectrum (EI Mass): 454 (M)
(ii) NMR Spectrum (in CDCl$_3$):

| δ: | 0.9 | (3H, CH$_3$—) |
|---|---|---|
|  | 1.2~1.8 | (20H, —(CH$_2$)$_4$—, OCH$_2$C$\underline{H}_3$ × 4) |
|  | 2.6 | (2H, —CH$_2$—⫞$_O$ ) |
|  | 4.0~4.4 | (8H, OC$\underline{H}_2$CH$_3$ × 4) |
|  | 4.5 | (1H, CH⟨$_P^P$ ) |
|  | 5.5 | (1H, H in isoxazole ring) |

Starting Compound: 3-Amino-5-n-hexylisoxazole

EXAMPLE 17:

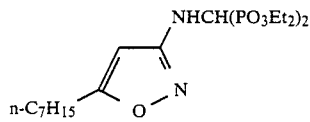

Tetraethyl [(5-n-heptyl-3-isoxazolyl)amino]methylene-bis(phosphonate)

Physico-chemical property:
(i) Mass Spectrum (EI Mass): 468 (M)
(ii) NMR Spectrum (in CDCl$_3$):

| δ: | 0.9 | (3H, CH₃—) |
|---|---|---|
| | 1.1~1.8 | (22H, —(CH₂)₅—, OCH₂CH₃ × 4) |
| | 2.6 | (2H, —CH₂—\|=\|_O_) |
| | 4.0~4.4 | (8H, OCH₂CH₃ × 4) |
| | 4.5 | (1H, CH(P)(P)) |
| | 5.5 | (1H, H in isoxazole ring) |

Starting compound: 3-Amino-5-n-heptylisoxazole

EXAMPLE 18:

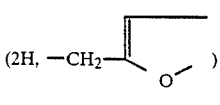

Tetraethyl [(5-n-octyl-3-isoxazolyl)amino]methylene-bis(phosphonate)

Physico-chemical property:
(i) Mass Spectrum (FAB Mass): 483 (M+1)
(ii) NMR Spectrum (in CDCl₃):

| δ: | 0.9 | (3H, CH₃—) |
|---|---|---|
| | 1.2~1.8 | (24H, —(CH₂)₆—, OCH₂CH₃ × 4) |
| | 2.6 | (2H, —CH₂—\|=\|_O_) |
| | 4.0~4.4 | (8H, OCH₂CH₃ × 4) |
| | 4.5 | (1H, CH(P)(P)) |
| | 5.5 | (1H, H in isoxazole ring) |

Starting compound: 3-Amino-5-n-octylisoxazole

EXAMPLE 19:

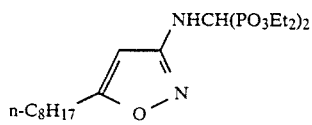

Tetraethyl [(5-isoamyl-3-isoxazolyl)amino]methylene-bis(phosphonate)

Physico-chemical property:
(i) Mass Spectrum (FAB Mass): 441 (M+1)
(ii) NMR Spectrum

| δ: | 0.9 | (6H, (CH₃)₂—) |
|---|---|---|
| | 1.2~1.7 | (17H, CH(CH₃)₂—, OCH₂CH₃ × 4) |
| | 2.6 | (2H, CH₂—\|=\|_O_) |
| | 4.0~4.4 | (8H, OCH₂CH₃ × 4) |
| | 4.5 | (1H, CH(P)(P)) |
| | 5.6 | (1H, H in isoxazole ring) |

Starting compound: 3-Amino-5-isoamylisoxazole

EXAMPLE 20:

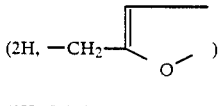

Tetraethyl [(5-p-methoxyphenethyl-3-isoxazolyl)amino]-methylene-bis(phosphonate)

Physico-chemical property:
(i) Mass Spectrum (EI Mass): 504 (M)
(ii) NMR Spectrum (in CDCl₃):

| δ: | 1.2~1.4 | (12H, OCH₂CH₃ × 4) |
|---|---|---|
| | 2.9 | (3H, OMe) |
| | 3.8 | (4H, —CH₂CH₂—) |
| | 4.0~4.4 | (8H, OCH₂CH₃ × 4) |
| | 4.5 | (1H, CH(P)(P)) |
| | 5.5 | (1H, H in isoxazole ring) |
| | 6.8, 7.1 | (4H, H in benzene ring) |

Starting compound: 3-Amino-5-p-methoxyphenethylisoxazole

EXAMPLE 21:

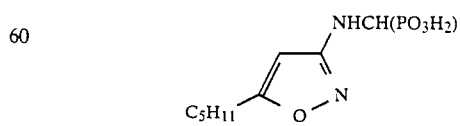

A solution of 3 g of tetraethyl [(5-n-pentyl-3-isoxazolyl)amino]methylene-bis(phosphonate) in 30 ml of concentrated hydrochloric acid was heated under reflux for 3 hours. After the reaction mixture was concentrated, the solid obtained was washed with acetonitrile to give 1.8 g of [(5-n-pentyl-3-isoxazolyl)amino]methylene-bis(phosphonic acid) as a solid.

This had the following physico-chemical property.

(i) Elementary Analysis (as $C_9H_{18}N_2O_7P_2$):

|  | C (%) | H (%) | N (%) | P (%) |
|---|---|---|---|---|
| Calculated: | 32.94 | 5.53 | 8.54 | 18.88 |
| Found: | 32.88 | 5.36 | 8.56 | 18.86 |

(ii) Mass Spectrum (FAB Mass): 327 (M−1)

(iii) NMR Spectrum (in $D_2O$ with $K_2CO_3$):

| δ: | 0.9 | (3H, $CH_3$) |
|---|---|---|
|  | 1.3~1.8 | (6H, $-(CH_2)_3-$) |
|  | 2.6 | (2H, $-CH_2-$ ) |
|  | 3.8 | (1H, $-CH\langle^P_P$ ) |
|  | 5.8 | (1H, H- ) |

In the same manner as Example 21, the following compounds were prepared.

EXAMPLE 22:

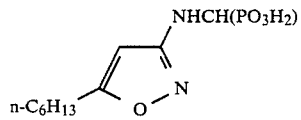

[(5-n-hexyl-3-isoxazolyl)amino]methylene-bis(phosphonic acid)

Physico-chemical property:
(i) m.p.: 238° C. (decomposition)
(ii) Elementary Analysis (as $C_{10}H_{20}N_2O_7P_2$):

|  | C (%) | H (%) | N (%) | P (%) |
|---|---|---|---|---|
| Calculated: | 35.10 | 5.89 | 8.19 | 18.10 |
| Found: | 35.38 | 5.72 | 8.11 | 17.84 |

(iii) Mass Spectrum (FAB Mass): 343 (M+1)

EXAMPLE 23:

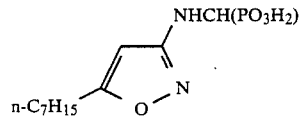

Physico-chemical property:
(i) m.p.: 205° C. (decomposition)
(ii) Elementary Analysis (as $C_{11}H_{22}N_2O_7P_2$):

|  | C (%) | H (%) | N (%) | P (%) |
|---|---|---|---|---|
| Calculated: | 37.09 | 6.22 | 7.86 | 17.39 |
| Found: | 37.09 | 6.15 | 7.83 | 17.28 |

(iii) Mass Spectrum (FAB Mass): 357 (M+1)

EXAMPLE 24:

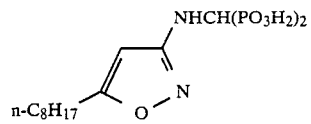

Physico-chemical property:
(i) m.p.: 225° C. (decomposition)
(ii) Elementary Analysis (as $C_{12}H_{24}N_2O_7P_2$):

|  | C (%) | H (%) | N (%) |
|---|---|---|---|
| Calculated: | 38.93 | 6.53 | 7.57 |
| Found: | 38.93 | 6.51 | 7.64 |

(iii) Mass Spectrum (FAB Mass): 371 (M+1)

EXAMPLE 25:

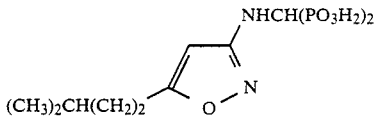

Physico-chemical property:
(i) m.p.: 196° C. (decomposition)
(ii) Elementary Analysis (as $C_9H_{18}N_2O_7P_2$):

|  | C (%) | H (%) | N (%) | P (%) |
|---|---|---|---|---|
| Calculated: | 32.94 | 5.53 | 8.54 | 18.88 |
| Found: | 32.66 | 5.50 | 8.66 | 18.72 |

(iii) Mass Spectrum (FAB Mass): 329 (M+1)

EXAMPLE 26:

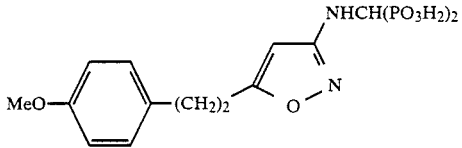

Physico-chemical property:
(i) m.p.: 265° C. (decomposition)
(ii) Elementary Analysis (as $C_{13}H_{18}N_2O_8P_2$):

|  | C (%) | H (%) | N (%) | P (%) |
|---|---|---|---|---|
| Calculated: | 39.81 | 4.62 | 7.14 | 15.79 |
| Found: | 39.69 | 4.46 | 7.19 | 15.71 |

(iii) Mass Spectrum (FAB Mass): 392 (M+1)

EXAMPLE 27:

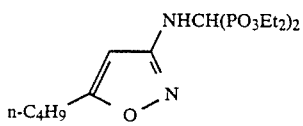

A mixture of 3 g of 3-amino-5-n-butylisoxazole, 3.7 g of ethyl orthoformate and 12 g of diethyl phosphite was heated at 150° C. with stirring for 60 minutes. The reaction mixture was concentrated under reduced pressure, and the resulting residue was purified on a silicagel column (eluent: 0 to 3% ethanol-chloroform) to give 5 g of tetraethyl [(5-n-butyl-3-isoxazolyl)amino]methylene-bis(phosphonate) as a pale yellow oil.

The physico-chemical characteristics of this product are as follows:
(i) Mass Spectrum (FAB Mass): 247 (M+1)
(ii) NMR Spectrum (in CDCl$_3$):

| δ: | 0.9 | (3H, CH$_3$—) |
|---|---|---|
| | 1.2~1.8 | (16H, —(CH$_2$)$_2$—, OCH$_2$CH$_3$ × 4) |
| | 2.6 | (2H, —CH$_2$—⟨ring⟩) |
| | 4.0~4.4 | (8H, OCH$_2$CH$_3$ × 4) |
| | 4.5 | (1H, CH(P)(P)) |
| | 5.5 | (1H, H in isoxazole ring) |

EXAMPLE 28:

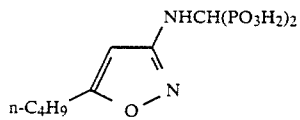

A solution of 4.8 g of tetraethyl [(5-n-butyl-3-isoxazolyl)amino]methylene-bis(phosphonate) in 50 ml of concentrated hydrochloric acid was heated under reflux for 3 hours. After the reaction mixture was concentrated, the solid obtained was washed with acetonitrile to give 2.5 g of [(5-n-butyl-3-isoxazolyl)amino]methylene-bis(phosphonic acid) as a solid.

This had the following physico-chemical property.
(i) m.p.: 200° C. (decomposition)
(ii) Elementary Analysis (as C$_8$H$_{16}$N$_2$O$_7$P$_2$):

| | C (%) | H (%) | N (%) | P (%) |
|---|---|---|---|---|
| Calculated: | 30.58 | 5.13 | 8.91 | 19.72 |
| Found: | 30.28 | 4.84 | 8.95 | 19.52 |

(iii) Mass Spectrum (FAB Mass): 315 (M+1)

EXAMPLE 29:

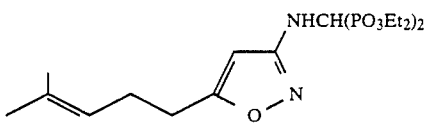

A mixture of 3.3 g of 3-amino-5-(4-methyl-3-ene)pentylisoxazole, 4.4 g of ethyl orthoformate and 20 g of diethyl phosphite was heated at 150° C. with stirring for 60 minutes. The reaction mixture was concentrated under reduced pressure, and the resulting residue was purified on a silicagel column (eluent: 0 to 3% methanol-chloroform) to give 3.6 g of tetraethyl [[5-(4-methyl-3-ene)pentyl-3-isoxazolyl]amino]methylene-bis(phosphonate) as a pale yellow oil.

The physico-chemical characteristics of this product are as follows:
(i) Mass Spectrum (EI Mass): 452 (M)
(ii) NMR Spectrum (in CDCl$_3$):

| δ: | 1.6~1.7 | (6H, CH$_3$\ /CH$_3$ ⟩=) |
|---|---|---|
| | 5.6 | (1H, H in isoxazole ring) |

In the same manner as Example 29, the following compounds were produced.

EXAMPLE 30:

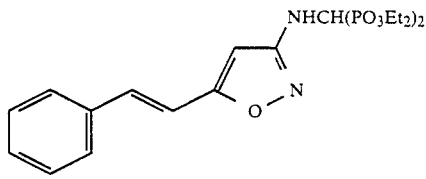

Physico-chemical property:
(i) Mass Spectrum (EI Mass): 472 (M)
(ii) NMR Spectrum:

| δ: | 5.9 | (1H,H in isoxazole ring) |
|---|---|---|
| | 6.7~7.5 | (1H,H based on styrene) |

Starting compound: 3-Amino-5-styrylisoxazole

EXAMPLE 31:

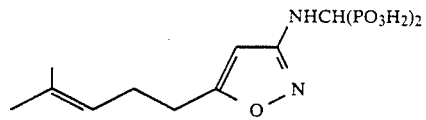

Iodotrimethylsilane (6.2 g) was added dropwise to an ice-cold solution of 3.5 g of tetraethyl [[5-(4-methyl-3-ene)pentyl-3-isoxazolyl]amino]methylene-bis(phosphonate) in 35 ml of carbon tetrachloride. Then the temperature was allowed to rise to room temperature, and the mixture was stirred for 1 hour. The reaction mixture was concentrated, methanol was then added, and the mixture was again concentrated. The residue thus obtained was washed with acetone and acetonitrile to give 1.8 g of [[5-(4-methyl-3-ene)pentyl-3-isoxazolyl-]amino]methylene-bis(phosphonic acid) as a solid.

The physico-chemical characteristics of this product are as follows:
This has the following physico-chemical property.
(i) m.p.: 213° C. (decomposition)
(ii) Elementary Analysis (as $C_{10}H_{18}N_2O_7P_2$):

|  | C (%) | H (%) | N (%) | P (%) |
|---|---|---|---|---|
| Calculated: | 35.30 | 5.33 | 8.23 | 18.21 |
| Found: | 35.19 | 5.23 | 8.30 | 18.05 |

(iii) Mass Spectrum (FAB Mass): 341 (M+1)

In the same manner as Example 31, the following compounds were prepared.

EXAMPLE 32:

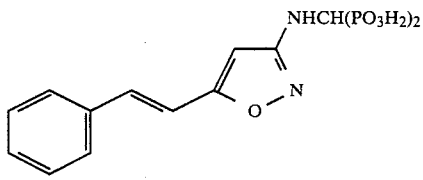

Physico-chemical property:
(i) m.p.: 287° C. (decomposition)
(ii) Elementary Analysis (as $C_{12}H_{14}N_2O_7P_2$):

|  | C (%) | H (%) | N (%) | P (%) |
|---|---|---|---|---|
| Calculated: | 40.01 | 3.92 | 7.78 | 17.20 |
| Found: | 39.73 | 3.96 | 7.61 | 17.46 |

(iii) Mass Spectrum (FAB Mass): 459 (M−1)

EXAMPLE 33:

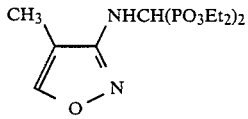

A mixture of 2.9 g of 3-amino-4-methylisoxazole, 5.7 g of ethyl orthoformate and 20.4 g of diethyl phosphite was heated at 160° C. with stirring for 3 hours. The reaction mixture was concentrated under reduced pressure, and the resulting residue was purified on a silicagel column (eluent: chloroform-ethyl acetate) to give 3.2 g of tetraethyl [(4-methyl-3-isoxazolyl)amino]methylene-bis(phosphonate) as a solid.
m.p.: 68°–69° C.

EXAMPLE 34:

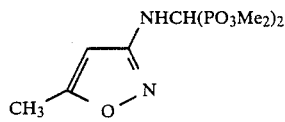

To an ice-cold solution of 9.8 g of 3-amino-5-methylisoxazole in dichloromethane (98 ml) was added dropwise 40 ml of a mixture of formic acid/acetic anhydride (5:3). Then the mixture was stirred overnight at room temperature. The reaction mixture was concentrated, and the solid obtained was washed with ether to give 10 g of 5-methylisoxazolyl-3-formamide.

A mixture of 9.8 ml of trimethyl phosphite and 1.3 ml of phosphorus trichloride was heated at 65° C. for 30 minutes. To this reaction mixture was added 1 g of 5-methylisoxazolyl-3-formamide, and the mixture was stirred at that temperature for 1 hour. The reaction mixture was concentrate and subjected to purification on a silica gel column (eluent: chloroform-methanol) to give 0.9 g of tetramethyl [(5-methyl-3-isoxazolyl-)amino]methylene-bis(phosphonate) as crystals.

The physico-chemical characteristics of this product are as follows:
(i) Mass Spectrum (FAB Mass): 329 (M+1)
(ii) NMR Spectrum (in CDCl$_3$):

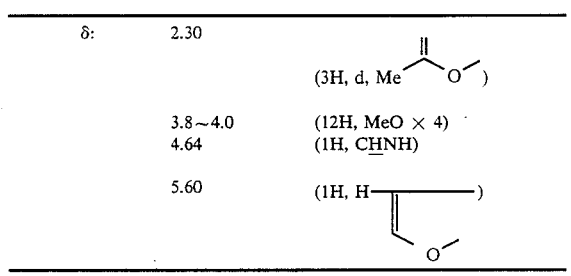

In the same manner as Example 34, the compounds of Examples 2 to 5, 10, 15 to 20, 27, 29, 30 and 33 can also be prepared.

MANUFACTURE EXAMPLE 1:

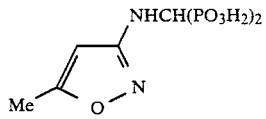

Iodotrimethylsilane (7.1 ml) was added dropwise to an ice-cold solution of 4.8 g of tetraethyl [(5-methyl-3-isoxazolyl)amino]methylene-bis(phosphonate) in 90 ml of carbon tetrachloride. Then the temperature was allowed to rise to room temperature, and the mixture was stirred for 1 hour. The reaction mixture was concentrated, methanol was then added, and the mixture was again concentrated. The solid thus obtained was washed with a hot acetone to give 2.9 g of [(5-methyl-3-isoxazolyl)amino]methylene-bis(phosphonic acid) as a colorless solid.

The physico-chemical characteristics of this product are as follows.
(i) Elementary Analysis (as $C_5H_{10}N_2O_7P_2$):

|  | C (%) | H (%) | N (%) |
|---|---|---|---|
| Calculated: | 22.07 | 3.70 | 10.30 |
| Found: | 22.13 | 3.80 | 9.96 |

(ii) Mass Spectrum (FAB Mass): 273 (M+1)
(iii) NMR Spectrum (in D$_2$O):

| δ: | 2.30 | (3H, d, Me in isoxazole ring) |
|---|---|---|
|  | 4.08 | (1H, t, NHCH) |
|  | 5.88 | (1H, d, H in isoxazole ring) |

MANUFACTURE EXAMPLE 2:

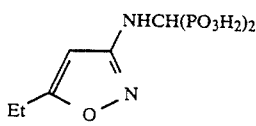

A solution of 4.9 g of tetraethyl [(5-ethyl-3-isoxazolyl)amino]methylene-bis(phosphonate) in 46 ml of concentrated hydrochloric acid was heated under reflux for 3 hours. After the reaction mixture was concentrated, the solid obtained was washed with acetone to give 2.8 g of [(5-ethyl-3-isoxazolyl)amino]methylene-bis(phosphonic acid) as a solid.

This had the following physico-chemical property:
(i) Elementary Analysis (as $C_6H_{12}N_2O_7P_2$):

|  | C (%) | H (%) | N (%) |
|---|---|---|---|
| Calculated: | 25.19 | 4.23 | 9.79 |
| Found: | 24.89 | 4.30 | 9.55 |

(ii) Mass Spectrum (FAB Mass): 287 (M+1)
(iii) NMR Spectrum (in $D_2O$):

| δ: | 1.20 | (3H, —$CH_2CH_3$) |
|---|---|---|
|  | 2.64 | (2H, —$CH_2CH_3$) |
|  | 4.10 | (1H, —NHCH—) |
|  | 5.90 | (1H, H is isoxazole ring) |

MANUFACTURE EXAMPLE 3:

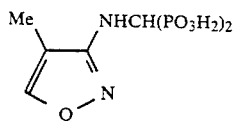

A solution of 3.2 g of tetraethyl [(4-methyl-3-isoxazolyl)amino]methylene-bis(phosphonate) in 32 ml of concentrated hydrochloric acid was heated under reflux for 4 hours. After the reaction mixture was concentrated, the solid obtained was washed with a mixture of methanol-acetonitrile-acetone to give 1.8 g of [(4-methyl-3-isoxazolyl)amino]methylene-bis(phosphonic acid) as a solid.

(i) m.p.: 272°–274° C. (decomposition)
(ii) Elementary Analysis (as $C_5H_{10}N_2O_7P_2$):

|  | C (%) | H (%) | N (%) |
|---|---|---|---|
| Calculated: | 22.07 | 3.70 | 10.30 |
| Found: | 21.90 | 3.70 | 9.99 |

PRESCRIPTION EXAMPLE:

Examples for prescription of the compound of the present invention as a drug will be mentioned below.
(1) Tablet:

| Compound of Manufacture Example 1 | 5 mg |
|---|---|
| Lactose | 119 mg |
| Corn Starch | 67 mg |
| Hydroxypropyl Cellulose | 4 mg |
| Calcium Carboxymethyl Cellulose | 4 mg |
| Magnesium Stearate | 1 mg |
| Total | 200 mg |

5 g of the compound of Manufacture Example 1, 119 g of lactose and 67 g of corn starch were uniformly blended, 40 ml of an aqueous 10% (w/w) hydroxypropyl cellulose solution was added thereto, and the resulting mixture was wet-granulated. The granules thus obtained were blended with 4 g of calcium carboxymethyl cellulose and 1 g of magnesium stearate, and the resulting mixture is formed into tablets, each having a weight of 200 mg/tablet.

(2) Capsule:

| Compound of Manufacture Example 1 | 5 mg |
|---|---|
| Crystalline Cellulose | 50 mg |
| Crystalline lactose | 144 mg |
| Magnesium Stearate | 1 mg |
| Total | 200 mg |

The above-mentioned ingredients were blended each in an amount of 1000 times of the above-mentioned amount and encapsulant in gelatin capsules, each containing 200 mg of the mixture per one capsule.

We claim:

1. Bisphosphonic acid derivatives of the formula:

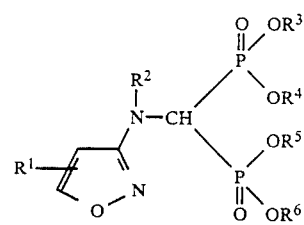

in which $R^1$ represents an alkyl group having from 5 to 10 carbon atoms, a cycloalkyl group having from 3 to 10 carbon atoms, a phenyl group, an alkenyl group having from 2 to 10 carbon atoms, which may be substituted by a phenyl group or a phenyl substituted alkyl group having from 1 to 5 carbon atoms, which may be substituted by an alkoxy group having from 1 to 5 carbon atoms;

$R^2$ represents a hydrogen atom or an alkanoyl group having from 2 to 6 carbon atoms; and $R^3$, $R^4$, $R^5$ and $R^6$ may be the same or different, each represents a hydrogen atom or an alkyl group having from 1 to 5 carbon atoms, or pharmaceutically acceptable salts thereof.

2. Bisphosphonic acid derivatives of the formula:

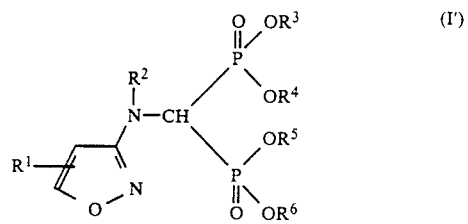

(I')

in which
$R^1$ represents an alkyl group having from 5 to 10 carbon atoms;

$R^2$ represents a hydrogen atom or an alkanoyl group having from 2 to 6 carbon atoms; and $R^3$, $R^4$, $R^5$ and $R^6$ may be the same or different, each represents a hydrogen atom or an alkyl group having from 1 to 5 carbon atoms, or pharmaceutically acceptable salts thereof.

3. Bisphosphonic acid derivatives or the salts thereof as claimed in claim 2, wherein $R^1$ in the Formula (1') represents a pentyl group.

4. The compound as claimed in claim 2, wherein said compound is [(5-n-pentyl-3-isoxazolyl)amino]methyl-bis(phosphonic acid) or the salt thereof.

5. The compound as claimed in claim 2, wherein said compound is tetraethyl [(5-n-pentyl-3-isoxazolyl)amino]methylene-bis(phosphonate).

6. Bisphosphonic acid derivatives of the formula:

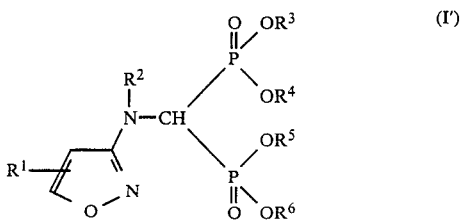
(I')

in which $R^1$ represents a cycloalkyl group having from 3 to 10 carbon atoms, a phenyl group, an alkenyl group having from 2 to 10 carbon atoms which may be substituted by a phenyl group or a phenyl substituted alkyl group having from 1 to 5 carbon atoms which may be substituted by an alkoxy group having from 1 to 5 carbon atoms;

$R^2$ represents a hydrogen atom or an alkanoyl group having from 2 to 6 carbon atoms;

$R^3$, $R^4$, $R^5$ and $R^6$ may be the same or different, each represents a hydrogen atom or an alkyl group having from 1 to 5 carbon atoms; or pharmaceutically acceptable salts thereof.

7. Bisphosphonic acid derivatives of the formula:

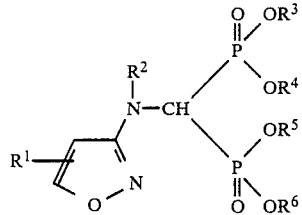
(I')

in which $R^1$ represents a cycloalkyl group having from 3 to 10 carbon atoms, $R^2$ represents a hydrogen atom or an alkanoyl group having from 2 to 6 carbon atoms;

$R^3$, $R^4$, $R^5$ and $R^6$ may be the same or different, each represents a hydrogen atom or an alkyl group having from 1 to 5 carbon atoms; or pharmaceutically acceptable salts thereof.

8. The compound as claimed in claim 7, wherein said compound is [(5-cyclopropyl-3-isoxazolyl)amino]-methylene-bis(phosphonic acid) or the salt thereof.

9. The compound as claimed in claim 7, wherein said compound is tetraethyl [(5-cyclopropyl-3-isoxazolyl)amino]methylene-bis(phosphonate).

10. A pharmaceutical composition comprising a pharmaceutically effective amount of a compound of claim 1 and a carrier therefor.

11. The pharmaceutical composition as claimed in claim 10, wherein $R^1$ in formula (I) represents a phentyl group or a cyclopropyl group.

12. The pharmaceutical composition as claimed in claim 10, wherein the compound of formula (I) is [(5-n-pentyl-3-isoxazolyl)-amino]-methylene-bis(phosphonic acid) or a salt thereof.

13. The pharmaceutical composition as claimed in claim 10, wherein the compound of formula (I) is tetraethyl [(5-n-pentyl-3-isoxazolyl)amino]methylene-bis(phosphonate).

14. The pharmaceutical composition as claimed in claim 10, wherein the compound of formula (I) is [(5-cyclopropyl-3-isoxazolyl)amino]-methylene-bis(phosphonic acid) or a salt thereof.

15. The pharmaceutical composition as claimed in claim 10, wherein the compound of formula (I) is tetraethyl [(5-cyclopropyl-3-isoxazolyl)amino]methylene-bis(phosphonate).

* * * * *

UNITED STATES PATENT AND TRADEMARK OFFICE
CERTIFICATE OF CORRECTION

PATENT NO. : 4,973,576

DATED : November 27, 1990

INVENTOR(S) : Shuichi Sakamoto, et al.

It is certified that error appears in the above-identified patent and that said Letters Patent is hereby corrected as shown below:

Abstract:
  Line 2: After the formula: "$R^2$" should read --$R^1$--

Column 29, line 61: under the formula should read:
--[(5-n-heptyl-3-isoxazolyl)amino]methylene-bis(phosphonic acid)--

Column 30, line 15: under the formula should read:
--[(5-n-octyl-3-isoxazolyl)amino]methylene-bis(phosphonic acid)--

Column 30, line 36: under the formula should read:
--[(5-isoamyl-3-isoxazolyl)amino]methylene-bis(phosphonic acid)--

Column 30, line 57: under the formula should read:
--[(5-p-methoxyphenethyl-3-isoxazolyl)amino]methylene-bis(phosphonic acid)--

Column 32, line 43: under the formula should read:
--Tetraethyl [(5-styryl-3-isoxazolyl)amino]methylene-bis(phosphonate)--

UNITED STATES PATENT AND TRADEMARK OFFICE
CERTIFICATE OF CORRECTION

PATENT NO. : 4,973,576

DATED : November 27, 1990

INVENTOR(S) : Shuichi Sakamoto, et al.

It is certified that error appears in the above-identified patent and that said Letters Patent is hereby corrected as shown below:

Column 32, line 43: under the formula should read: --Tetraethyl [(5-styryl-3-isoxazolyl)amino]methylene-bis(phosphonate)--

Signed and Sealed this

Fourth Day of August, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,973,576
DATED : November 27, 1990
INVENTOR(S) : Sakamoto et al.

It is certified that error appears in the above-identified patent and that said Letters Patent is hereby corrected as shown below:

Column 19, line 5, and Column 12, line 35: the formula should read:

Column 38, line 31: "phentyl" should read --pentyl--

Signed and Sealed this

Twenty-fourth Day of August, 1993

*Attest:*

BRUCE LEHMAN

*Attesting Officer*    Commissioner of Patents and Trademarks